US010443066B2

(12) United States Patent
Chittoor et al.

(10) Patent No.: US 10,443,066 B2
(45) Date of Patent: Oct. 15, 2019

(54) PLANT REGULATORY ELEMENTS AND USES THEREOF

(71) Applicant: Monsanto Technology LLC, St. Louis, MO (US)

(72) Inventors: Jaishree M. Chittoor, Wildwood, MO (US); Stanislaw Flasinski, Ballwin, MO (US); Mohammed Oufattole, Wildwood, MO (US); Michael W. Petersen, Sauk City, WI (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/453,779

(22) Filed: Mar. 8, 2017

(65) Prior Publication Data

US 2017/0260541 A1 Sep. 14, 2017

Related U.S. Application Data

(60) Provisional application No. 62/306,790, filed on Mar. 11, 2016.

(51) Int. Cl.
*C12N 15/82* (2006.01)
*C07K 14/415* (2006.01)

(52) U.S. Cl.
CPC ........ *C12N 15/8216* (2013.01); *C07K 14/415* (2013.01)

(58) Field of Classification Search
None
See application file for complete search history.

(56) References Cited

U.S. PATENT DOCUMENTS

| 5,489,520 | A | * | 2/1996 | Adams | A01H 4/00 536/23.7 |
| 5,500,365 | A | * | 3/1996 | Fischhoff | C07K 14/005 435/418 |
| 2015/0135362 | A1 | | 5/2015 | Flasinski et al. | |

FOREIGN PATENT DOCUMENTS

| WO | WO 01/44457 A2 | * | 6/2001 |
| WO | WO 2012/158535 | | 11/2012 |

OTHER PUBLICATIONS

Potenza et al., In Vitro Cell Dev Biol Plant 40:1-22 (2004).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Saha et al., In Silica Biol 7(1):7-19 (2007).*
Odell et al., Nature 313:810-12 (1985).*
Garcia-Mas et al., "The genome of melon (*Cucumis melo* L.)," PNAS 109(29):11872-11877, 2012.
GenBank Accession No. BE324177, last updated Dec. 21, 2000.
GenBank Accession No. JG523938, last updated Jun. 13, 2011.
GenBank Accession No. JG534947, last updated Jun. 13, 2011.
GenBank Accession No. LN681851, dated Mar. 5, 2015.
GenBank Accession No. LN681858, dated Mar. 5, 2015.
International Search Report and Written Opinion regarding International Application No. PCT/US2017/021310, dated Aug. 10, 2017.
Krishnakumar et al., "MTGD: The *Medicago truncatula* Genome Database," *Plant Cell Physiol.* 56(1):e1, 2015.
GenBank AC174287.13, "Medicago truncatula clone mth2-32a8, complete sequence," Available at https://www.ncbi.nlm.nih.gov/nuccore/117949867/, Retrieved Apr. 24, 2017.
GenBank CT571263.1, "Medicago truncatula chromosome 5 clone mte1-7c20, Complete Sequence," Available at https://www.ncbi.nlm.nih.gov/nuccore/CT571263.1, Retrieved Apr. 24, 2017.
GenBank CT573354.6, "M.truncatula DNA sequence from clone MTH2-18N13 on chromosome 3, complete sequence," Available at https://www.ncbi.nlm.nih.gov/nuccore/CT573354.6, Retrieved Apr. 24, 2017.
GenBank CU013540.5, "Medicago truncatula chromosome 3 clone MTH2-48A16, Working Draft Sequence," Available at https://www.ncbi.nlm.nih.gov/nuccore/CU013540.5, Retrieved Apr. 24, 2017.
NCBI Reference Sequence XM_003599210.2, "Medicago truncatula photosystem II 5 kDa protein mRNA," Available at https://www.ncbi.nlm.nih.gov/nuccore/922377859, Retrieved Apr. 24, 2017.
NCBI Reference Sequence XM_003617900.2, "Medicago truncatula light-harvesting complex I chlorophyll A/B-binding protein mRNA," Available at https://www.ncbi.nlm.nih.gov/nuccore/XM_003617900, Retrieved Apr. 24, 2017.
Tang et al., "An improved genome release (version Mt4.0) for the model legume *Medicago truncatula*," *Bmc Genomics* 15:312; 2014.
Young et al., "The *Medicago* genome provides insight into the evolution of rhizobial symbioses," *Nature* 480(7378):520-524; 2011.
Partial Supplementary European Search Report regarding European Application No. 17763976.2, dated Jun. 28, 2019.
Dutton et al., "Studies on the Two Ferredoxins from Pisum sativum," *Biocehmical Society Transactions*:6(6);1217-1218,1978.
Anonymous, "AT4G21090 (MFDX2)," Retrieved from the Internet: URL: https://www.arabidopsis.org/servlets/TairObiect?id=128355 &type=locus [retrieved on Jun. 13, 2019], 2013.

* cited by examiner

*Primary Examiner* — Russell T Boggs
(74) *Attorney, Agent, or Firm* — Dentons US LLP; Carine Marie Doyle, Esq.

(57) ABSTRACT

The invention provides recombinant DNA molecules and constructs, as well as their nucleotide sequences, useful for modulating gene expression in plants. The invention also provides transgenic plants, plant cells, plant parts, and seeds comprising the recombinant DNA molecules operably linked to heterologous transcribable DNA molecules, as are methods of their use.

16 Claims, No Drawings
Specification includes a Sequence Listing.

SEQUENCE LISTING

```
<160> NUMBER OF SEQ ID NOS: 18

<210> SEQ ID NO 1
<211> LENGTH: 2001
<212> TYPE: DNA
<213> ORGANISM: Cucumis melo
<220> FEATURE:
<221> NAME/KEY: misc_feature
<222> LOCATION: (1)..(2001)
<223> OTHER INFORMATION: EXP sequence derived from a Cucumis melo
      putative Ferredoxin 2 protein gene comprised of a promoter
      operably linked 5' to its native leader.

<400> SEQUENCE: 1
ttgtttgttt ctttatagta gatgatgttt tcaaatatag aaaatgagct aatgtttctt      60
ttaaatatag taaaatttta ctttctatcc atgaaaaact gtgatagatt ccaaatagtc     120
aactattact ttagtgatcg atagaaagta attcttcatt cttattgcat tctttgttat     180
ggttccttgg gtgcaatttt atccaacaag ttccaaatct tcaaagaaaa gatttttttt     240
ttaatttata actattttta gggccagtgt caatttataa atctaaattt taagttatat     300
caattcaaac tttgaacttt aattatctgg ataatgagta cattctcgat gcagaggata     360
atgaaaggat caactttcca tactctatca tgtaaagcat gagcatgttc ttgtgtacga     420
aaattaaaat caatataaga taatttagta aataaagacg acttaaatta tcatttaaat     480
atatcaatag tttcactctc actttacaat tgcagaattc aaaataataa taataaaaaa     540
gaaatttaaa gagacaacgt gagtctaaat ctaacttatt atcgatatac attttcatca     600
acatatgtta aagactaaaa attcaatgat tcgaattttt gctcgtccta tcctactaaa     660
```

```
gaaacctcat gtgtcaattc actcaaatct gaaaagattc atccatttca actcctctct    720
atccattact aaccaaagca aaaattcaat gagagcagat tgaagtttcc acccttgtct    780
taagaagaat gtctacacaa tgtcctaatt tttaatgtag tgcgttttta ttagttacaa    840
acaatttagt gggatccact catcatataa atgaaaaaaa gaaatactc atacaaattc     900 atcgttatga cacaagtagc cacccataga caatattctc tttatgaatt agttattgtt    960
tgatcattta gtttccgaaa cttatatttt gagcaattga gatttgaatt taggtttgat   1020
ttaattcctt aagttttga aagtgatatt taattctttc gagttttaag atgaatttct    1080
aaatagtttc tagataagtc tacaactagc taatataaca aaatggcgac gtgatagtta   1140
gatatgttat ttagactttt ttaaactgct aattcaaatt gataagaaag ttagaccgca   1200
aggattttat agtacaatag gattggagga atttgaatca caagctccaa agtcacatta   1260
gcacatcctt aatgttagct gaactacttt tgcaaaaatg aaaactcgat tatgaaaaaa   1320
aagttcaaat cttgtgtact tgtgtaatgt cctaagttta ggtggggcca tgaatgaatt   1380
aggatcatga cttttgattg aaatagatct aagaacatga aagtataatt aagaaaaact   1440
taaaagaatc aaattttact acatatacca acaatgtgca ttttcctctt gaatgactca   1500
atcatagaaa ctaaaaagca tgcggtgtta gtttgtggta ccaataactt ttactcttag   1560
aagcaatcta agacgaacaa ggatggcatt gttaaatcat agggataaag aggaatgttg   1620
agaccattag agatcgaatc tagattccaa accctactaa atacttgagc ttgggcatta   1680
catctagaga ccagaagtgt attttgttta tttattatta ttttatttga aaaaaaagg    1740 aacaaaatgg tttatgaagc cattagtact ttaagcggct gttgttcata ttttgaaacc   1800
aaatctttgg aaggataaga acccacaacc attaccattc attgccaaga taaggcctta   1860
actcacaacc acacgctctc tatttcactc tgcacgttat agccacacga cccaaatatc   1920
ctctttaaaa aaccctcttc actctctcaa ttccatttca tctcatctca tctccaatcc   1980
aacacaaaaa caagaagaaa a                                            2001
```

<210> SEQ ID NO 2
<211> LENGTH: 1936
<212> TYPE: DNA
<213> ORGANISM: Cucumis melo
<220> FEATURE:
<221> NAME/KEY: misc_feature
<222> LOCATION: (1)..(1936)
<223> OTHER INFORMATION: Promoter sequence derived from a Cucumis melo
      putative Ferredoxin 2 protein gene.

<400> SEQUENCE: 2

```
ttgtttgttt ctttatagta gatgatgttt tcaaatatag aaaatgagct aatgtttctt     60
ttaaatatag taaaatttta ctttctatcc atgaaaaact gtgatagatt ccaaatagtc    120
aactattact ttagtgatcg atagaaagta attcttcatt cttattgcat tctttgttat    180
ggttccttgg gtgcaatttt atccaacaag ttccaaatct tcaaagaaaa gatttttttt    240
ttaatttata actattttta gggccagtgt caatttataa atctaaattt taagttatat    300
caattcaaac tttgaacttt aattatctgg ataatgagta cattctcgat gcagaggata    360
atgaaaggat caactttcca tactctatca tgtaaagcat gagcatgttc ttgtgtacga    420
aaattaaaat caatataaga taatttagta aataaagacg acttaaatta tcatttaaat    480
atatcaatag tttcactctc actttacaat tgcagaattc aaaataataa taataaaaaa    540
gaaatttaaa gagacaacgt gagtctaaat ctaacttatt atcgatatac attttcatca    600
```

```
acatatgtta aagactaaaa attcaatgat tcgaattttt gctcgtccta tcctactaaa    660
gaaacctcat gtgtcaattc actcaaatct gaaaagattc atccatttca actcctctct    720
atccattact aaccaaagca aaaattcaat gagagcagat tgaagtttcc acccttgtct    780
taagaagaat gtctacacaa tgtcctaatt tttaatgtag tgcgttttta ttagttacaa    840
acaatttagt gggatccact catcatataa atgaaaaaaa gaaatactc atacaaattc     900 atcgttatga cacaagtagc cacccataga caatattctc tttatgaatt agttattgtt    960
tgatcattta gtttccgaaa cttatatttt gagcaattga gatttgaatt taggtttgat   1020
ttaattcctt taagttttga aagtgatatt taattctttc gagttttaag atgaatttct   1080
aaatagtttc tagataagtc tacaactagc taatataaca aaatggcgac gtgatagtta   1140
gatatgttat ttagactttt ttaaactgct aattcaaatt gataagaaag ttagaccgca   1200
aggattttat agtacaatag gattggagga atttgaatca caagctccaa agtcacatta   1260
gcacatcctt aatgttagct gaactacttt tgcaaaaatg aaaactcgat tatgaaaaaa   1320
aagttcaaat cttgtgtact tgtgtaatgt cctaagttta ggtggggcca tgaatgaatt   1380
aggatcatga cttttgattg aaatagatct aagaacatga aagtataatt aagaaaaact   1440
taaaagaatc aaattttact acatatacca acaatgtgca ttttcctctt gaatgactca   1500
atcatagaaa ctaaaaagca tgcggtgtta gtttgtggta ccaataactt ttactcttag   1560
aagcaatcta agacgaacaa ggatggcatt gttaaatcat agggataaag aggaatgttg   1620
agaccattag agatcgaatc tagattccaa accctactaa atacttgagc ttgggcatta   1680
catctagaga ccagaagtgt attttgttta tttattatta ttttatttga aaaaaaagg    1740 aacaaaatgg tttatgaagc cattagtact ttaagcggct gttgttcata ttttgaaacc   1800
aaatctttgg aaggataaga acccacaacc attaccattc attgccaaga taaggcctta   1860
actcacaacc acacgctctc tatttcactc tgcacgttat agccacacga cccaaatatc   1920
ctctttaaaa aaccct                                                    1936
```

<210> SEQ ID NO 3
<211> LENGTH: 65
<212> TYPE: DNA
<213> ORGANISM: Cucumis melo
<220> FEATURE:
<221> NAME/KEY: misc_feature
<222> LOCATION: (1)..(65)
<223> OTHER INFORMATION: Leader sequence derived from a Cucumis melo
      putative Ferredoxin 2 protein gene.

<400> SEQUENCE: 3

```
cttcactctc tcaattccat ttcatctcat ctcatctcca atccaacaca aaaacaagaa     60
gaaaa                                                                 65
```

<210> SEQ ID NO 4
<211> LENGTH: 2001
<212> TYPE: DNA
<213> ORGANISM: Cucumis melo
<220> FEATURE:
<221> NAME/KEY: misc_feature
<222> LOCATION: (1)..(2001)
<223> OTHER INFORMATION: EXP sequence derived from a Cucumis melo
      chlorophyll a-b binding protein 13 gene comprised of a promoter
      operably linked 5' to its native leader.

<400> SEQUENCE: 4

```
aaaacccaaa taaatacaaa gttaatagat tttcaacaat gcggggatag ctcagttggg      60
agagcgtcag actgaagatc tgaaggtcgc gtgttcgatc cacgctcacc gcatcttttt     120
tttgttctgt ttttcccagc gaatgaacta ccatacgtc gtcgtttgta tagccatgat     180
ccatgaagcg ctctaattac caatcatttt ttctttcttg gaattgatca agttacaaat     240
ataaaattat tttacactaa aaactctctt ttaaaaattt agatccaatt ttaattttgt     300
tttctaaaag attgtatcca agaagtaaaa tttacatgga aaataaaatg cctataaatt     360
aaaaaatgtt atattttcgt gacctttaac cttaggaaca tttgataact attactttga     420
gattgcagtc ataggcaaca caaggtcttg gacaaacatg ttcgtgacac caaacacccc     480
cctcaaaatt aagtatatta taccaactca tttcatttgc ttgttacggt tgtgttttat     540
caatccttcc tcgtcttgtt ttttcctcca aatttgtaat cttaaaattg gtgaaacatc     600
acatatttga ttctcaatct tagattttct accttttagg taatctatat tttgaaattg     660
aaattgaaat tgaattccgt gtaaaatcta aatatggga acccaattcg aatttaatgt     720
tttatgtaaa ggccaataat gttccaaatt tatttcctta ttattattgt atattttgtc     780
cccaagtaca tcatagattg gctttcaatt ccaaatccat catggtatat ttttaggtgc     840
aaactattgt cgtagattta atccctagt tttgttgatt tttaaaata gtactttcaa     900
caattttaaa ttttatttga ttggttataa acttcgggtg tgatttagtt gtccaatttg     960
gattatattg tcattttcat acataaattt atttattttt gaaaaagtta tcttttagtc    1020
tttgaaattg aaattttat gaatatgtgg atttagtccc tcaattctca aattaaccat    1080
cttcacaaga gtgagaaaca gagatgggag ggagaaaaat ggaagataa aaaaagtatt    1140
tttcttcctc catgttatta ggtcacatca atatttataa tatttatat taaatttaat    1200
gatttctttt gggagaggta ctcttagacc tatttttta acaaaaatta ttggactcat    1260
aatttttta ttgtcccttta atttctttta tttgtatcta gacttataa agtttgagag    1320
ttttatattt taaggagaaa tatattaaaa tataaggtta gttttcatac actagataga    1380
cttatgatct tatacgagtg aatgagttaa actctcaatt aaaattattt gaattttttc    1440
aaaaattaaa atcatccatt ttgttaaatt aaaatttgaa gaaatttata ggatgcgtaa    1500
gaattgatgc cttgttaatt ttcaaatata attatagtaa aaattcttaa ttagtttact    1560
aacaacgatt taaaagttta ctttgatgtg ttgaacaata tttatcaaac caaatttgat    1620
caagtggata tactaacaaa agttcaagat cttaaacttt aagtgaatta attttgacat    1680
atatatatat ataaaaaaaa aaagttaggt gttaaaagaa aactgaaaat tgttaaaaga    1740
aaagaaaagg agggtataga taaaatgtgg atagaaagag atgagttgta gatgcaaaaa    1800
aatctttaga aacaatatga ttggctaact aagccctctc attccccac aaaatttctc    1860
atatctttca ctcttcacca ctcatctcct cgtttcctca taatattccc ccacttccac    1920
tctctctcac acaatctcca acactactgc ccattcctct gttctttctc tctactctca    1980
accacagagc ttcaagtacc c                                              2001
```

<210> SEQ ID NO 5
<211> LENGTH: 1899
<212> TYPE: DNA
<213> ORGANISM: Cucumis melo
<220> FEATURE:
<221> NAME/KEY: misc_feature
<222> LOCATION: (1)..(1899)
<223> OTHER INFORMATION: Promoter sequence derived from a Cucumis melo chlorophyll a-b binding protein 13 gene.

<400> SEQUENCE: 5

```
aaaacccaaa taaatacaaa gttaatagat tttcaacaat gcggggatag ctcagttggg      60
agagcgtcag actgaagatc tgaaggtcgc gtgttcgatc cacgctcacc gcatcttttt     120
tttgttctgt ttttcccagc gaatgaacta tccatacgtc gtcgtttgta tagccatgat     180
ccatgaagcg ctctaattac caatcatttt ttctttcttg gaattgatca agttacaaat     240
ataaaattat tttacactaa aaactctctt ttaaaaattt agatccaatt ttaattttgt     300
tttctaaaag attgtatcca agaagtaaaa tttacatgga aaataaaatg cctataaatt     360
aaaaaatgtt atattttcgt gacctttaac cttaggaaca tttgataact attactttga     420
gattgcagtc ataggcaaca caaggtcttg gacaaacatg ttcgtgacac caaacacccc     480
cctcaaaatt aagtatatta taccaactca tttcatttgc ttgttacggt tgtgttttat     540
caatccttcc tcgtcttgtt ttttcctcca aatttgtaat cttaaaattg gtgaaacatc     600
acatatttga ttctcaatct tagattttct acctttaaggg taatctatat tttgaaattg     660
aaattgaaat tgaattccgt gtaaaatcta taatatggga acccaattcg aatttaatgt     720
tttatgtaaa ggccaataat gttccaaatt tatttcctta ttattattgt atattttgtc     780
cccaagtaca tcatagattg gctttcaatt ccaaatccat catggtatat ttttaggtgc     840
aaactattgt cgtagattta atcccctagt tttgttgatt ttttaaaata gtactttcaa     900
caattttaaa ttttatttga ttggttataa acttcgggtg tgatttagtt gtccaatttg     960
gattatattg tcattttcat acataaattt atttattttt gaaaagtta tcttttagtc    1020
tttgaaattg aaatttttat gaatatgtgg atttagtccc tcaattctca aattaaccat    1080
cttcacaaga gtgagaaaca gagatgggag ggagaaaaat ggaaagataa aaaaagtatt    1140
tttcttcctc catgttatta ggtcacatca atatttataa tattttatat taaatttaat    1200
gatttctttt gggagaggta ctcttagacc tattttttta acaaaaatta ttggactcat    1260
aattttttaa ttgtcccttta atttcttttta tttgtatcta gactttataa agtttgagag    1320
ttttatattt taaggagaaa tatattaaaa tataaggtta gttttcatac actagataga    1380
cttatgatct tatacgagtg aatgagttaa actctcaatt aaaattattt gaattttttc    1440
aaaaattaaa atcatccatt ttgttaaatt aaaatttgaa gaaatttata ggatgcgtaa    1500
gaattgatgc cttgttaatt ttcaaatata attatagtaa aaattcttaa ttagtttact    1560
aacaacgatt taaaagttta ctttgatgtg ttgaacaata tttatcaaac caaatttgat    1620
caagtggata tactaacaaa agttcaagat cttaaacttt aagtgaatta attttgacat    1680
atatatatat ataaaaaaaa aaagttaggt gttaaaagaa aactgaaaat tgttaaaaga    1740
aaagaaaagg agggtatag taaaatgtgg atagaaagag atgagttgta gatgcaaaaa    1800
aatcttaga aacaatatga ttggctaact aagccctctc attaccccac aaaatttctc    1860
atatctttca ctcttcacca ctcatctcct cgtttcctc                           1899
```

<210> SEQ ID NO 6
<211> LENGTH: 102
<212> TYPE: DNA
<213> ORGANISM: Cucumis melo

```
<220> FEATURE:
<221> NAME/KEY: misc_feature
<222> LOCATION: (1)..(102)
<223> OTHER INFORMATION: Leader sequence derived from a Cucumis melo
      chlorophyll a-b binding protein 13 gene.

<400> SEQUENCE: 6
ataatattcc cccacttcca ctctctctca cacaatctcc aacactactg cccattcctc    60
tgttctttct ctctactctc aaccacagag cttcaagtac cc                      102

<210> SEQ ID NO 7
<211> LENGTH: 1014
<212> TYPE: DNA
<213> ORGANISM: Cucumis melo
<220> FEATURE:
<221> NAME/KEY: misc_feature
<222> LOCATION: (1)..(1014)
<223> OTHER INFORMATION: EXP sequence derived from a Cucumis melo B-box
      zinc finger protein 24-like gene comprised of a promoter operably
      linked 5' to its native leader.

<400> SEQUENCE: 7 aggcttttc gatctaaaat cacctgtaac aagtttaata atcgagaatt agtgaaagtg     60
tacctatttt aaaatagtaa ttagtatttt attcaataga tatgtttgaa atctaaaaaa   120
ttctcttata acttggaaat ttagataaca atgatgcaaa ccgcaaaaga gtatatacta   180
aacattgaat aaactattag cttaatactc taaaatcagt ggttggaaaa aaaacttcca   240
cttacattta cgtgaaaagc gtcaaaatta agaaaaatca tttgttacaa tcacacataa   300
ataattctaa gcactctttt ttcactatta gattagagaa taccagaaaa aaatttgatt   360
tgagttagta cactttgaga tgaaaacatt tataactaga acaatttgaa ataaagtaag   420
atgttccatt tatagggcat cgaatctatg actattttgt ttttttggtg agttaaatgg   480
gatgaggaat cggaaaagaa agagcatttg attactacaa gaagagtttg ttgtttccca   540
tcgtacaaaa tcaatcgata gtgtgttgtt gttcgttgtt catccctaaa caaaaagaga   600
tggtgtgaag aatcaaaagc atttagctaa ttttttagag ctcctaaatt cctcagccac   660
aaaccaacgg agcttcacag ccacacaaat ggcctcctct ctttttccgcc ttgttgtctc   720 caccatcttt cttgattttg atttccctga atcctcaacc cttatcccct cacccaccct   780
tctctttcct tcttcaatcc tccacctttt acttctcttt ctctatcccc ttctttctcc   840
attcttattc tctaatccc acttttcctc ttcttcttcc cttccatctc tccggcgcca   900
ctgttctact ggcggtttaa tttcatgggt tcttcttgat cttggagtag gaaacaggga   960
agtggagttt cggcgaatct attcaaaatc ttagtggttg ttcagaggga gaag        1014

<210> SEQ ID NO 8
<211> LENGTH: 815
<212> TYPE: DNA
<213> ORGANISM: Cucumis melo
<220> FEATURE:
<221> NAME/KEY: misc_feature
<222> LOCATION: (1)..(815)
<223> OTHER INFORMATION: Promoter sequence derived from a Cucumis melo
      B-box zinc finger protein 24-like gene.

<400> SEQUENCE: 8 aggcttttc gatctaaaat cacctgtaac aagtttaata atcgagaatt agtgaaagtg     60
tacctatttt aaaatagtaa ttagtatttt attcaataga tatgtttgaa atctaaaaaa   120
ttctcttata acttggaaat ttagataaca atgatgcaaa ccgcaaaaga gtatatacta   180
```

| | |
|---|---|
| aacattgaat aaactattag cttaatactc taaaatcagt ggttggaaaa aaaacttcca | 240 |
| cttacattta cgtgaaaagc gtcaaaatta agaaaaatca tttgttacaa tcacacataa | 300 |
| ataattctaa gcactctttt ttcactatta gattagagaa taccagaaaa aaatttgatt | 360 |
| tgagttagta cactttgaga tgaaaacatt tataactaga acaatttgaa ataaagtaag | 420 |
| atgttccatt tatagggcat cgaatctatg actattttgt ttttttggtg agttaaatgg | 480 |
| gatgaggaat cggaaaagaa agagcatttg attactacaa gaagagtttg ttgtttccca | 540 |
| tcgtacaaaa tcaatcgata gtgtgttgtt gttcgttgtt catccctaaa caaaaagaga | 600 |
| tggtgtgaag aatcaaaagc atttagctaa tttttagag ctcctaaatt cctcagccac | 660 |
| aaaccaacgg agcttcacag ccacacaaat ggcctcctct cttttccgcc ttgttgtctc | 720 |
| caccatcttt cttgattttg atttccctga atcctcaacc cttatcccct cacccaccct | 780 |
| tctctttcct tcttcaatcc tccacctttt acttc | 815 |

```
<210> SEQ ID NO 9
<211> LENGTH: 199
<212> TYPE: DNA
<213> ORGANISM: Cucumis melo
<220> FEATURE:
<221> NAME/KEY: misc_feature
<222> LOCATION: (1)..(199)
<223> OTHER INFORMATION: Leader sequence derived from a Cucumis melo B-
      box zinc finger protein 24-like gene.

<400> SEQUENCE: 9
```

| | |
|---|---|
| tctttctcta tccccttctt tctccattct tattctctaa tacccacttt tcctcttctt | 60 |
| cttcccttcc atctctccgg cgccactgtt ctactggcgg tttaatttca tgggttcttc | 120 |
| ttgatcttgg agtaggaaac agggaagtgg agtttcggcg aatctattca aaatcttagt | 180 |
| ggttgttcag agggagaag | 199 |

```
<210> SEQ ID NO 10
<211> LENGTH: 1887
<212> TYPE: DNA
<213> ORGANISM: Medicago truncatula
<220> FEATURE:
<221> NAME/KEY: misc_feature
<222> LOCATION: (1)..(1887)
<223> OTHER INFORMATION: EXP sequence derived from a Medicago truncatula
      light harvesting complex protein b2 gene comprised of a promoter
      operably linked 5' to its native leader.

<400> SEQUENCE: 10
```

| | |
|---|---|
| agtagtagta ggtgttgaca tttctttttt ttttgaacaa gaggagttga catttctaag | 60 |
| gtggctttgt taccacttga tagacttta gaatgtatgt caataagaat agaaaagaac | 120 |
| acaggtggtt taaattttga tctgaatgag acaatatttg catgaagtaa agtttagatt | 180 |
| tcaaatatgc atacttaatg tgtctattgt gatatttaag gcatcattca tctctcttgc | 240 |
| ctcttgccct cggtatatat gtatcggacc ataaagggaa ccaaaaatga tttcagatac | 300 |
| ataaaattaa ttttcacatg tttaagtaat ctcaattgaa atggatttta ttccatcatt | 360 |
| aattctaaca tgaaattata tgtagttttt aactccaaac ataatttctc acttgtccac | 420 |
| taacatatta attaacattg tcattccaaa agaaaaacaa aactgaatag aggtggagat | 480 |
| caacatgtga cttgaattat acatgtacgg ttgagaatta tattaaaaat ctaaagttgg | 540 |
| ggtcaacttg tgaaatagat tctcttcatt gtatttttt cacatttgat attatatagg | 600 |
| atagttgtga attgtgaaat tagataacca cgtgagccaa ttttgtaatt tagttgggat | 660 |

```
taactgccac cttgtgttct tgaggttgaa cagtttacag ccaagtcttc ctttgcctgt    720
ttgtcttgta catcttcata ttcacgtggt ttaagccact tattttcgtg ttttttttc    780 tctcttttct cttcaacata tagttgtaat aatagataat atagggtttg atatgttttt    840
agttcttata gtgtgtttta gcctcacatt ttttcttt cattgaccaa cagcatacac    900
ttttttttgt gtatatttta gagactaaag tgcaatgaaa tcttatttat atggaaataa    960
aaaaaatgag cattttttg ttagtgaata tgtatgcagg atttgaaaaa ggaatgagat   1020
tcggagcctg ttcttttcat gactcctctt aattgagaca tgaaattcaa tgcttgacgt   1080
aaggataagt gttctattca atacgcgtaa gaaaagaatg agcagttcag atcaaatcga   1140
actttttatt cttgtaattg taatgttatt tttcgggtca cacaattaag ttttgtttgc   1200
acattagtct gtaattcttc gggttattca catttcattt gatggtcaga ggcaaattga   1260
aagctaagca gtggtaattc taaagattcc cccgggaaaa aatagaaatg tctcctacgt   1320
tacctatact atgtgtaata tttaatttat tttgtcacat tgtatcaaat tagtttctca   1380
cattatgtac atttcaaaat gattcattaa attgcaatta aattcaccca tccgtttaac   1440
attaagttgg taatttctga gatgtatttg aaattattat gtaaacgaga tgcatttgat   1500
agcaaaataa aaagatgttg ctgttttca ctcaaactcc caatccaaac ccttccaagt   1560
ttctgtattt ctctcagctt tggtggacct aatttccttg gctcacattc acctctccaa   1620
aacatctaag caaccagatc aatgcatcca catggcacaa agagagccac aatatcacta   1680 caaatataa gcttgggaat ccacatacta attcaccacc aataagatgt tgctgacttg   1740
tgcatatcct aatctacaat atcttatgat ttccaccgtg gccactccca acacttctat   1800
aaacctttgt atcctttctt cattcttcac aacaacacta gcttatacca ctaaagagaa   1860
caaacatcaa gaaacctcaa cgccctc                                      1887
```

<210> SEQ ID NO 11
<211> LENGTH: 1837
<212> TYPE: DNA
<213> ORGANISM: Medicago truncatula
<220> FEATURE:
<221> NAME/KEY: misc_feature
<222> LOCATION: (1)..(1837)
<223> OTHER INFORMATION: Promoter sequence derived from a Medicago truncatula light harvesting complex protein b2 gene.

<400> SEQUENCE: 11

```
agtagtagta ggtgttgaca tttcttttt ttttgaacaa gaggagttga catttctaag     60
gtggctttgt taccacttga tagacttta gaatgtatgt caataagaat agaaaagaac    120
acaggtggtt taaattttga tctgaatgag acaatatttg catgaagtaa agtttagatt    180
tcaaatatgc atacttaatg tgtctattgt gatatttaag gcatcattca tctctcttgc    240
ctcttgccct cggtatatat gtatcggacc ataaagggaa ccaaaaatga tttcagatac    300
ataaaattaa ttttcacatg tttaagtaat ctcaattgaa atggatttta ttccatcatt    360
aattctaaca tgaaattata tgtagttttt aactccaaac ataatttctc acttgtccac    420
taacatatta attaacattg tcattccaaa agaaaaacaa aactgaatag aggtggagat    480
caacatgtga cttgaattat acatgtacgg ttgagaatta tattaaaaat ctaaagttgg    540
ggtcaacttg tgaaatagat tctcttcatt gtatttttt cacatttgat attatatagg    600
atagttgtga attgtgaaat tagataacca cgtgagccaa ttttgtaatt tagttgggat    660
taactgccac cttgtgttct tgaggttgaa cagtttacag ccaagtcttc ctttgcctgt    720
```

```
ttgtcttgta catcttcata ttcacgtggt ttaagccact tattttcgtg ttttttttc      780 tctcttttct cttcaacata tagttgtaat aatagataat atagggtttg atatgttttt      840
agttcttata gtgtgtttta gcctcacatt tttttctttt cattgaccaa cagcatacac      900
ttttttttgt gtatatttta gagactaaag tgcaatgaaa tcttatttat atggaaataa      960
aaaaaatgag cattttttg ttagtgaata tgtatgcagg atttgaaaaa ggaatgagat       1020
tcggagcctg ttcttttcat gactcctctt aattgagaca tgaaattcaa tgcttgacgt     1080
aaggataagt gttctattca atacgcgtaa gaaaagaatg agcagttcag atcaaatcga     1140 acttttatt cttgtaattg taatgttatt tttcgggtca cacaattaag ttttgtttgc      1200
acattagtct gtaattcttc gggttattca catttcattt gatggtcaga ggcaaattga     1260
aagctaagca gtggtaattc taaagattcc cccgggaaaa aatagaaatg tctcctacgt     1320
tacctatact atgtgtaata tttaatttat tttgtcacat tgtatcaaat tagtttctca    1380
cattatgtac atttcaaaat gattcattaa attgcaatta aattcaccca tccgtttaac    1440
attaagttgg taatttctga gatgtatttg aaattattat gtaaacgaga tgcatttgat    1500
agcaaaataa aaagatgttg ctgttttca ctcaaactcc caatccaaac ccttccaagt     1560
ttctgtattt ctctcagctt tggtggacct aatttccttg gctcacattc acctctccaa    1620
aacatctaag caaccagatc aatgcatcca catggcacaa agagagccac aatatcacta    1680
caaaatataa gcttgggaat ccacatacta attcaccacc aataagatgt tgctgacttg    1740
tgcatatcct aatctacaat atcttatgat ttccaccgtg gccactccca acacttctat    1800 aaaccctttgt atcctttctt cattcttcac aacaaca                            1837

<210> SEQ ID NO 12
<211> LENGTH: 50
<212> TYPE: DNA
<213> ORGANISM: Medicago truncatula
<220> FEATURE:
<221> NAME/KEY: misc_feature
<222> LOCATION: (1)..(50)
<223> OTHER INFORMATION: Leader sequence derived from a Medicago
      truncatula light harvesting complex protein b2 gene.

<400> SEQUENCE: 12
ctagcttata ccactaaaga gaacaaacat caagaaacct caacgccctc                 50

<210> SEQ ID NO 13
<211> LENGTH: 594
<212> TYPE: DNA
<213> ORGANISM: Medicago truncatula
<220> FEATURE:
<221> NAME/KEY: misc_feature
<222> LOCATION: (1)..(594)
<223> OTHER INFORMATION: EXP sequence derived from a Medicago truncatula
      photosystem II chloroplast precursor gene comprised of a promoter
      operably linked 5' to its native leader.

<400> SEQUENCE: 13
ttactgttgg ttttggctaa atttgttatg ttgtgctatc tgttgagaaa aatgttgggt     60
agcttatatt actccatatc agataagcct gacctcactc ccattagaag gaaacaaata   120
tattaaagta caatattcat ttttttttgg gaatagatta attttgatgc attttcggtg   180
taaaacattt tacatgctca acaaatctca aaccatcttt tgtatgactt tttggattta   240
agatagatat gataaaagtc aaatatttta atgatccaat agttatcatt gattgtcttg   300
tacaaaattt ttcacactgcc ggtacctatt agcatctttc ttatccttta aattcacatt  360
aattaacaag catcaacaca agccccccaa aaccatttct agcattatca actattcaac   420
```

```
gtggcattaa cttattggtc atatcattaa tgagataaga taatgtatgg tcctacccta    480
ccacaaaagc tcccattttt gtatgattta cattccatat attcattctt ccacttgccc    540
acaatagaag ctatcacata gagactagtt cagaatccag atcacattgt agaa          594
```

```
<210> SEQ ID NO 14
<211> LENGTH: 552
<212> TYPE: DNA
<213> ORGANISM: Medicago truncatula
<220> FEATURE:
<221> NAME/KEY: misc_feature
<222> LOCATION: (1)..(552)
<223> OTHER INFORMATION: Promoter sequence derived from a Medicago
      truncatula photosystem II chloroplast precursor gene.

<400> SEQUENCE: 14
ttactgttgg ttttggctaa atttgttatg ttgtgctatc tgttgagaaa aatgttgggt     60
agcttatatt actccatatc agataagcct gacctcactc ccattagaag gaaacaaata   120
tattaaagta caatattcat ttttttttgg gaatagatta attttgatgc attttcggtg   180
taaaacattt tacatgctca acaaatctca aaccatcttt tgtatgactt tttggattta   240
agatagatat gataaaagtc aaatatttta atgatccaat agttatcatt gattgtcttg   300
tacaaaattt ttacactgcc ggtacctatt agcatctttc ttatcccttta aattcacatt   360 aattaacaag catcaacaca agccccccaa aaccatttct agcattatca actattcaac   420
gtggcattaa cttattggtc atatcattaa tgagataaga taatgtatgg tcctacccta   480
ccacaaaagc tcccattttt gtatgattta cattccatat attcattctt ccacttgccc   540
acaatagaag ct                                                      552
```

```
<210> SEQ ID NO 15
<211> LENGTH: 42
<212> TYPE: DNA
<213> ORGANISM: Medicago truncatula
<220> FEATURE:
<221> NAME/KEY: misc_feature
<222> LOCATION: (1)..(42)
<223> OTHER INFORMATION: Leader sequence derived from a Medicago
      truncatula photosystem II chloroplast precursor gene.

<400> SEQUENCE: 15
atcacataga gactagttca gaatccagat cacattgtag aa                       42
```

```
<210> SEQ ID NO 16
<211> LENGTH: 1797
<212> TYPE: DNA
<213> ORGANISM: Medicago truncatula
<220> FEATURE:
<221> NAME/KEY: misc_feature
<222> LOCATION: (1)..(1797)
<223> OTHER INFORMATION: Enhancer sequence derived from a Medicago
      truncatula light harvesting complex protein b2 gene.

<400> SEQUENCE: 16
agtagtagta ggtgttgaca tttcttttt ttttgaacaa gaggagttga catttctaag      60
gtggctttgt taccacttga tagacttta gaatgtatgt caataagaat agaaaagaac    120
acaggtggtt taaattttga tctgaatgag acaatatttg catgaagtaa agtttagatt   180
tcaaatatgc atacttaatg tgtctattgt gatatttaag gcatcattca tctctcttgc   240
ctcttgccct cggtatatat gtatcggacc ataaagggaa ccaaaaatga tttcagatac   300
ataaaattaa ttttcacatg tttaagtaat ctcaattgaa atggatttta ttccatcatt   360
```

```
aattctaaca tgaaattata tgtagttttt aactccaaac ataatttctc acttgtccac      420
taacatatta attaacattg tcattccaaa agaaaaacaa aactgaatag aggtggagat      480
caacatgtga cttgaattat acatgtacgg ttgagaatta tattaaaaat ctaaagttgg      540
ggtcaacttg tgaaatagat tctcttcatt gtattttttt cacatttgat attatatagg      600
atagttgtga attgtgaaat tagataacca cgtgagccaa ttttgtaatt tagttgggat      660
taactgccac cttgtgttct tgaggttgaa cagtttacag ccaagtcttc ctttgcctgt      720
ttgtcttgta catcttcata ttcacgtggt ttaagccact tattttcgtg ttttttttc      780 tctcttttct cttcaacata tagttgtaat aatagataat atagggtttg atatgttttt      840
agttcttata gtgtgtttta gcctcacatt ttttctttt cattgaccaa cagcatacac      900 tttttttttgt gtatatttta gagactaaag tgcaatgaaa tcttatttat atggaaataa      960
aaaaaatgag cattttttg ttagtgaata tgtatgcagg atttgaaaaa ggaatgagat     1020
tcggagcctg ttctttttcat gactcctctt aattgagaca tgaaattcaa tgcttgacgt     1080
aaggataagt gttctattca atacgcgtaa gaaaagaatg agcagtttcag atcaaatcga     1140 actttttatt cttgtaattg taatgttatt tttcgggtca cacaattaag ttttgtttgc     1200
acattagtct gtaattcttc gggttattca catttcattt gatggtcaga ggcaaattga     1260
aagctaagca gtggtaattc taaagattcc cccgggaaaa aatagaaatg tctcctacgt     1320
tacctatact atgtgtaata tttaatttat tttgtcacat tgtatcaaat tagtttctca     1380
cattatgtac atttcaaaat gattcattaa attgcaatta aattcaccca tccgtttaac     1440
attaagttgg taatttctga gatgtatttg aaattattat gtaaacgaga tgcatttgat     1500
agcaaaataa aaagatgttg ctgttttca ctcaaactcc caatccaaac ccttccaagt     1560
ttctgtattt ctctcagctt tggtggacct aatttccttg gctcacattc acctctccaa     1620
aacatctaag caaccagatc aatgcatcca catggcacaa agagagccac aatatcacta     1680
caaaatataa gcttgggaat ccacatacta attcaccacc aataagatgt tgctgacttg     1740
tgcatatcct aatctacaat atcttatgat ttccaccgtg gccactccca acacttc          1797

<210> SEQ ID NO 17
<211> LENGTH: 2001
<212> TYPE: DNA
<213> ORGANISM: Artificial
<220> FEATURE:
<223> OTHER INFORMATION: Coding sequence for beta-glucuronidase (GUS)
      with a processable intron.

<400> SEQUENCE: 17
atggtccgtc ctgtagaaac cccaacccgt gaaatcaaaa aactcgacgg cctgtgggca       60
ttcagtctgg atcgcgaaaa ctgtggaatt gatcagcgtt ggtgggaaag cgcgttacaa      120
gaaagccggg caattgctgt gccaggcagt tttaacgatc agttcgccga tgcagatatt      180
cgtaattatg cgggcaacgt ctggtatcag cgcgaagtct ttataccgaa aggttgggca      240
ggccagcgta tcgtgctgcg tttcgatgcg gtcactcatt acggcaaagt gtgggtcaat      300
aatcaggaag tgatggagca tcagggcggc tatacgccat ttgaagccga tgtcacgccg      360
tatgttattg ccgggaaaag tgtacgtaag tttctgcttc tacctttgat atatatataa      420
taattatcat taattagtag taatataata tttcaaatat tttttttcaaa ataaaagaat      480 gtagtatata gcaattgctt ttctgtagtt tataagtgtg tatattttaa tttataactt      540
```

```
ttctaatata tgaccaaaat ttgttgatgt gcaggtatca ccgtttgtgt gaacaacgaa      600
ctgaactggc agactatccc gccgggaatg gtgattaccg acgaaaacgg caagaaaaag      660
cagtcttact tccatgattt ctttaactat gccggaatcc atcgcagcgt aatgctctac      720
accacgccga acacctgggt ggacgatatc accgtggtga cgcatgtcgc gcaagactgt      780
aaccacgcgt ctgttgactg gcaggtggtg gccaatggtg atgtcagcgt tgaactgcgt      840
gatgcggatc aacaggtggt tgcaactgga caaggcacta gcgggacttt gcaagtggtg      900
aatccgcacc tctggcaacc gggtgaaggt tatctctatg aactgtgcgt cacagccaaa      960
agccagacag agtgtgatat ctacccgctt cgcgtcggca tccggtcagt ggcagtgaag     1020
ggcgaacagt tcctgattaa ccacaaaccg ttctacttta ctggctttgg tcgtcatgaa     1080
gatgcggact tgcgtggcaa aggattcgat aacgtgctga tggtgcacga ccacgcatta     1140
atggactgga ttggggccaa ctcctaccgt acctcgcatt acccttacgc tgaagagatg     1200
ctcgactggg cagatgaaca tggcatcgtg gtgattgatg aaactgctgc tgtcggcttt     1260
aacctctctt taggcattgg tttcgaagcg ggcaacaagc cgaaagaact gtacagcgaa     1320
gaggcagtca acggggaaac tcagcaagcg cacttacagg cgattaaaga gctgatagcg     1380
cgtgacaaaa accacccaag cgtggtgatg tggagtattg ccaacgaacc ggataccegt     1440 ccgcaaggtg cacgggaata tttcgcgcca ctggcggaag caacgcgtaa actcgacccg     1500
acgcgtccga tcacctgcgt caatgtaatg ttctgcgacg ctcacaccga taccatcagc     1560
gatctctttg atgtgctgtg cctgaaccgt tattacggat ggtatgtcca aagcggcgat     1620
ttggaaacgg cagagaaggt actggaaaaa gaacttctgg cctggcagga gaaactgcat     1680
cagccgatta tcatcaccga atacggcgtg gatacgttag ccgggctgca ctcaatgtac     1740
accgacatgt ggagtgaaga gtatcagtgt gcatggctgg atatgtatca ccgcgtcttt     1800
gatcgcgtca gcgccgtcgt cggtgaacag gtatggaatt cgccgatttt gcgacctcg     1860 caaggcatat tgcgcgttgg cggtaacaag aaagggatct tcactcgcga ccgcaaaccg     1920
aagtcggcgg cttttctgct gcaaaaacgc tggactggca tgaacttcgg tgaaaaaccg     1980
cagcagggag gcaaacaatg a                                              2001
```

<210> SEQ ID NO 18
<211> LENGTH: 315
<212> TYPE: DNA
<213> ORGANISM: Gossypium barbadense
<220> FEATURE:
<221> NAME/KEY: misc_feature
<222> LOCATION: (1)..(315)
<223> OTHER INFORMATION: 3' UTR sequence derived from the Gossypium barbadense E6 gene.

<400> SEQUENCE: 18

```
tgatcacctg tcgtacagta tttctacatt tgatgtgtga tttgtgaaga acatcaaaca       60
aaacaagcac tggctttaat atgatgataa gtattatggt aattaattaa ttggcaaaaa      120
caacaatgaa gctaaaattt tatttattga gccttgcggt taatttcttg tgatgatctt      180
ttttttattt ttctaattat atatagtttc ctttgctttg aaatgctaaa ggtttgagag      240
agttatgctc ttttttttctt cctctttctt ttttaacttt atcatacaaa ttttgaataa      300
aaatgtgagt acatt                                                      315
```

US 10,443,066 B2

PLANT REGULATORY ELEMENTS AND USES THEREOF

REFERENCE TO RELATED APPLICATION

This application claims the benefit of U.S. provisional application No. 62/306,790, filed Mar. 11, 2016 which is herein incorporated by reference in its entirety.

INCORPORATION OF SEQUENCE LISTING

The sequence listing that is contained in the file named "MONS417US_sequencelisting.txt", which is 30,143 bytes (as measured in Microsoft Windows®) and was created on Mar. 8, 2017, is filed herewith by electronic submission, and is incorporated by reference herein.

FIELD OF THE INVENTION

The invention relates to the field of plant molecular biology; and plant genetic engineering. More specifically, the invention relates to DNA molecules useful for modulating gene expression in plants.

BACKGROUND

Regulatory elements are genetic elements that regulate gene activity by modulating the transcription of an operably linked transcribable DNA molecule. Such elements may include promoters, leaders, introns, and 3' untranslated regions and are useful in the field of plant molecular biology and plant genetic engineering.

SUMMARY OF THE INVENTION

The invention provides novel gene regulatory elements for use in plants. The invention also provides DNA constructs comprising the regulatory elements. The present invention also provides transgenic plant cells, plants, and seeds comprising the regulatory elements. In one embodiment, the regulatory elements are operably linked to a transcribable DNA molecule. In certain embodiments, the transcribable DNA molecule may be heterologous with respect to the regulatory sequence. Thus, a regulatory element sequence provided by the invention may, in particular embodiments, be defined as operably linked to a heterologous transcribable DNA molecule. The present invention also provides methods of making and using the regulatory elements, the DNA constructs comprising the regulatory elements, and the transgenic plant cells, plants, and seeds comprising the regulatory elements operably linked to a transcribable DNA molecule.

Thus, in one aspect, the invention provides a recombinant DNA molecule comprising a DNA sequence selected from the group consisting of: (a) a sequence with at least about 85 percent sequence identity to any of SEQ ID NOs: 1-15; (b) a sequence comprising any of SEQ ID NOs: 1-15; and (c) a fragment of any of SEQ ID NOs: 1-15, wherein the fragment has gene-regulatory activity; wherein the sequence is operably linked to a heterologous transcribable DNA molecule. By "heterologous transcribable DNA molecule," it is meant that the transcribable DNA molecule is heterologous with respect to the polynucleotide sequence to which it is operably linked. In specific embodiments, the recombinant DNA molecule comprises a DNA sequence having at least about 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs: 1-15. In particular embodiments, the DNA sequence comprises a regulatory element. In some embodiments the regulatory element comprises a promoter. In still other embodiments, the heterologous transcribable DNA molecule comprises a gene of agronomic interest, such as a gene capable of providing herbicide resistance in plants, or a gene capable of providing plant pest resistance in plants. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: (a) a sequence with at least about 85 percent sequence identity to any of SEQ ID NOs: 1-15; (b) a sequence comprising any of SEQ ID NOs: 1-15; and (c) a fragment of any of SEQ ID NOs: 1-15, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a monocotyledonous plant cell or a dicotyledonous plant cell.

In still yet another aspect, further provided herein is a transgenic plant, or part thereof, comprising a recombinant DNA molecule comprising a DNA sequence selected from the group consisting of: a) a sequence with at least 85 percent sequence identity to any of SEQ ID NOs: 1-15; b) a sequence comprising any of SEQ ID NOs: 1-15; and c) a fragment of any of SEQ ID NOs: 1-15, wherein the fragment has gene-regulatory activity; wherein the sequence is operably linked to a heterologous transcribable DNA molecule. In specific embodiments, the transgenic plant is a progeny plant of any generation that comprises the recombinant DNA molecule. A transgenic seed comprising the recombinant DNA molecule that produces such a transgenic plant when grown is also provided herein.

In another aspect, the invention provides a method of producing a commodity product comprising obtaining a transgenic plant or part thereof containing a recombinant DNA molecule of the invention and producing the commodity product therefrom. In one embodiment, the commodity product is processed seeds, grains, plant parts, oils and meal.

In still yet another aspect, the invention provides a method of producing a transgenic plant comprising a recombinant DNA molecule of the invention comprising transforming a plant cell with the recombinant DNA molecule of the invention to produce a transformed plant cell and regenerating a transgenic plant from the transformed plant cell.

BRIEF DESCRIPTION OF THE SEQUENCES

SEQ ID NO: 1 is a DNA sequence of a regulatory expression elements group (EXP) comprising a promoter derived from a *Cucumis melo* putative Ferredoxin 2 (Fe2) protein gene operably linked 5' to its native leader.

SEQ ID NO: 2 is a promoter sequence derived from a *Cucumis melo* putative Ferredoxin 2 (Fe2) protein gene.

SEQ ID NO: 3 is a leader sequence derived from a *Cucumis melo* putative Ferredoxin 2 (Fe2) protein gene.

SEQ ID NO: 4 is a DNA sequence of an EXP comprising a promoter derived from a *Cucumis melo* chlorophyll a-b binding protein 13 gene operably linked 5' to its native leader.

SEQ ID NO: 5 is a promoter sequence derived from a *Cucumis melo* chlorophyll a-b binding protein 13 gene.

SEQ ID NO: 6 is a leader sequence derived from a *Cucumis melo* chlorophyll a-b binding protein 13 gene.

SEQ ID NO: 7 is a DNA sequence of an EXP comprising a promoter derived from a *Cucumis melo* B-box zinc finger protein 24-like gene operably linked 5' to its native leader.

SEQ ID NO: 8 is a promoter sequence derived from a *Cucumis melo* B-box zinc finger protein 24-like gene.

SEQ ID NO: 9 is a leader sequence derived from a *Cucumis melo* B-box zinc finger protein 24-like gene.

SEQ ID NO: 10 is a DNA sequence of an EXP comprising a promoter derived from a *Medicago truncatula* light harvesting complex protein b2 gene operably linked 5' to its native leader.

SEQ ID NO: 11 is a promoter sequence derived from a *Medicago truncatula* light harvesting complex protein b2 gene.

SEQ ID NO: 12 is a leader sequence derived from a *Medicago truncatula* light harvesting complex protein b2 gene.

SEQ ID NO: 13 is a DNA sequence of an EXP comprising a promoter derived from a *Medicago truncatula* photosystem II chloroplast precursor gene operably linked 5' to its native leader.

SEQ ID NO: 14 is a promoter sequence derived from a *Medicago truncatula* photosystem II chloroplast precursor gene.

SEQ ID NO: 15 is a leader sequence promoter sequence derived from a *Medicago truncatula* photosystem II chloroplast precursor gene.

SEQ ID NO: 16 is an enhancer sequence derived from the promoter of the *Medicago truncatula* light harvesting complex protein b2 gene.

SEQ ID NO: 17 is a coding sequence for ß-glucuronidase (GUS) with a processable intron.

SEQ ID NO: 18 is a 3' UTR sequence derived from the *Gossypium barbadense* E6 gene.

DETAILED DESCRIPTION OF THE INVENTION

The invention provides DNA molecules having gene-regulatory activity in plants. The nucleotide sequences of these DNA molecules are provided as SEQ ID NOs: 1-15. These DNA molecules are capable of affecting the expression of an operably linked transcribable DNA molecule in plant tissues, and therefore regulating gene expression of an operably linked transgene in transgenic plants. The invention also provides methods of modifying, producing, and using the same. The invention also provides compositions that include transgenic plant cells, plants, plant parts, and seeds containing the recombinant DNA molecules of the invention, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases or a DNA molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation or gene editing.

As used herein, the term "sequence identity" refers to the extent to which two optimally aligned polynucleotide sequences or two optimally aligned polypeptide sequences are identical. An optimal sequence alignment is created by manually aligning two sequences, e.g., a reference sequence and another sequence, to maximize the number of nucleotide matches in the sequence alignment with appropriate internal nucleotide insertions, deletions, or gaps. As used herein, the term "reference sequence" refers to a DNA sequence provided as to a DNA sequence provided as SEQ ID NOs: 1-15.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a sequence that, when optimally aligned to a reference sequence, provided herein as SEQ ID NOs: 1-15, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence.

Regulatory Elements

Regulatory elements such as promoters, leaders (also known as 5' UTRs), enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are therefore useful for modifying plant phenotypes through genetic engineering.

As used herein, a "regulatory expression element group" or "EXP" sequence may refer to a group of operably linked regulatory elements, such as enhancers, promoters, leaders, and introns. Thus, a regulatory expression element group may be comprised, for instance, of a promoter operably linked 5' to a leader sequence. EXP's useful in practicing the present invention include 1, 4, 7, 10, and 13.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may be initially isolated from the 5' untranslated region (5' UTR) of a genomic copy of a gene. Alternately, promoters may be synthetically produced or manipulated DNA molecules. Promoters may also be chimeric. Chimeric promoters are produced through the fusion of two or more heterologous DNA molecules. Promoters useful in practicing the present invention include promoter elements comprised within any of SEQ ID NOs: 2, 5, 8, 11, and 14, or fragments or variants thereof. In specific embodiments of the invention, the claimed DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box, other known transcription factor binding site motif, or equivalent DNA sequence for recognition and binding of the RNA polymerase II complex for initiation of transcription.

In one embodiment, fragments of a promoter sequence disclosed herein are provided. Promoter fragments may comprise promoter activity, as described above, and may be useful alone or in combination with other promoters and promoter fragments, such as in constructing chimeric promoters, or in combination with other EXPs and EXP fragments. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. In certain embodiments, the invention provides fragments of any one of SEQ ID NOs: 1-15, having the activity of the full length sequence. Methods for producing such fragments from a starting promoter molecule are well known in the art.

Compositions derived from any of the promoter elements comprised within any of SEQ ID NOs: 2, 5, 8, 11, and 14, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Compositions derived from any of the promoter elements comprised within any of SEQ ID NOs: 2, 5, 8, 11, and 14 comprised of 3' deletions in which the TATA box element or equivalent sequence thereof and downstream sequence is removed can be used, for example, to make enhancer elements. Further deletions can be made to remove any elements that have positive or negative; tissue-specific; cell-specific; or timing-specific (such as, but not limited to, circadian rhythm) effects on expression. Any of the promoter elements comprised within any of SEQ ID NOs: 2, 5, 8, 11, and 14 and fragments or enhancers derived therefrom can be used to make chimeric transcriptional regulatory element compositions.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Leaders useful in practicing the present invention include SEQ ID NOs: 3, 6, 9, 12, and 15 or any of the leader elements comprised within any of SEQ ID NOs: 1, 4, 7, 10, and 13 or fragments or variants thereof. In specific embodiments, such DNA sequences may be defined as being capable of acting as a leader in a host cell, including, for example, a transgenic plant cell. In one embodiment, such sequences are decoded as comprising leader activity.

The leader sequences (also referred to as 5' UTRs) presented as SEQ ID NOs: 3, 6, 9, 12, and 15 or any of the leader elements comprised within any of SEQ ID NOs: 1, 4, 7, 10, and 13 may be comprised of regulatory elements, or may adopt secondary structures that can have an effect on transcription or translation of an operably linked transcribable DNA molecule. The leader sequences presented as SEQ ID NOs: 3, 6, 9, 12, and 15 or any of the leader elements comprised within any of SEQ ID NOs: 1, 4, 7, 10, and 13 can be used in accordance with the invention to make chimeric regulatory elements that affect transcription or translation of a an operably linked transcribable DNA molecule.

As used herein, the term "intron" refers to a DNA molecule that may be isolated or identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, IME in dicotyledonous plants has been shown by point mutations within the splice sites of the pat1 gene from *A. thaliana*. Multiple uses of the same intron in one plant have been shown to exhibit disadvantages. In those cases, it is necessary to have a collection of basic control elements for the construction of appropriate recombinant DNA elements.

As used herein, the terms "3' transcription termination molecule," "3' untranslated region" or "3' UTR" refer to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. The 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. The 3' UTR should not cause a reduction in the transcriptional activity imparted by the promoter, leader, enhancers, and introns that are used to drive expression of the DNA molecule. In plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

As used herein, the term "enhancer" or "enhancer element" refers to a cis-acting regulatory element, a.k.a. cis-element, which confers an aspect of the overall expression pattern, but is usually insufficient alone to drive transcription, of an operably linked transcribable DNA molecule. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression. An example of an enhancer element derived from the *Medicago truncatula* light harvesting complex protein b2 precursor gene promoter is provided as SEQ ID NO: 16.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; for example, the fusion of a promoter to an enhancer element. Thus, the design, construction, and use of chimeric promoters according to the methods disclosed herein for modulating the expression of operably linked transcribable DNA molecules are encompassed by the present invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, a DNA sequence provided as SEQ ID NOs: 1-15 may provide a regulatory element reference sequence, wherein the constituent elements that comprise the reference sequence may be joined by methods known in the art and may comprise substitutions, deletions, and/or insertions of one or more nucleotides or mutations that naturally occur in bacterial and plant cell transformation.

As used herein, the term "variant" refers to a second DNA molecule, such as a regulatory element, that is in composition similar, but not identical to, a first DNA molecule, and wherein the second DNA molecule still maintains the general functionality, i.e. the same or similar expression pattern, for instance through more or less equivalent transcriptional activity, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion, and/or insertion of one or more nucleotides of a reference sequence, wherein the derivative regulatory element has more or less or equivalent transcriptional or translational activity than the corresponding parent regulatory molecule. Regulatory element "variants" will also encompass variants arising from mutations that naturally occur in bacterial and plant cell transformation. In the present invention, a polynucleotide sequence provided as SEQ ID NOs: 1-15 may be used to create variants that are in similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast proteins.

Transcribable DNA Molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or are genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs: 1-15, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228,623; and U.S. Pat. Nos. 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA- mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding ß-glucuronidase (GUS), green fluorescent protein (GFP), proteins that confer antibiotic resistance, and proteins that confer herbicide tolerance. An example of a selectable marker transgene is provided as SEQ ID NO:17.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also include progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), gene editing (e.g., CRISPR-Cas systems), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, Calif., 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique*, (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NOs: 1-15. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Novel transcriptional regulatory elements and regulatory expression element groups (EXPs) were identified and cloned from genomic DNA of the dicot species *Cucumis melo* (WSH-39-1070AN) and *Medicago truncatula*.

Transcriptional regulatory elements were selected based upon proprietary and public microarray data derived from transcriptional profiling experiments conducted in soybean (*Glycine max*) and *Arabidopsis*, as well as homology based searches using known dicot sequences as queries against proprietary *Cucumis melo* and proprietary and public *Medicago truncatula* sequences.

Using the identified sequences, a bioinformatic analysis was conducted to identify regulatory elements within the amplified DNA. For example, bioinformatics analysis was performed to identify the transcriptional start site (TSS) and any bi-directionality, introns, or upstream coding sequence present in the sequence. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from *Cucumis melo* and *Medicago truncatula*. The resulting DNA fragments were ligated into base plant expression vectors using standard restriction enzyme digestion of compatible restriction sites and DNA ligation methods.

Analysis of the regulatory element TSS and intron/exon splice junctions can be performed using transformed plant tissue. Briefly, the plants are transformed with the plant expression vectors comprising the cloned DNA fragments operably linked to a heterologous transcribable DNA molecule. Next, the 5' RACE System for Rapid Amplification of cDNA Ends, Version 2.0 (Invitrogen, Carlsbad, Calif. 92008) is used to confirm the regulatory element TSS and intron/exon splice junctions by analyzing the DNA sequence of the produced mRNA transcripts.

The DNA sequences encoding the *Cucumis* and *Medicago* transcriptional regulatory expression element groups or EXP sequences which are comprised of a promoter element, operably linked to a leader element are presented in Table 1 along with their corresponding promoters and leaders.

TABLE 1

Transcriptional regulatory expression element groups, promoters, leaders and introns isolated from *Cucumis melo* and *Medicago truncatula*

| Description | SEQ ID NO: | Gene Annotation |
|---|---|---|
| EXP-CUCme.Fe2:1 | 1 | Putative Ferredoxin 2 (Fe2) protein |
| P-CUCme.Fe2:1 | 2 | Putative Ferredoxin 2 (Fe2) protein |
| L-CUCme.Fe2:1 | 3 | Putative Ferredoxin 2 (Fe2) protein |
| EXP-CUCme.CipLhcb:1 | 4 | Chlorophyll a-b binding protein 13 |
| P-CUCme.CipLhcb:1 | 5 | Chlorophyll a-b binding protein 13 |
| L-CUCme.CipLhcb:1 | 6 | Chlorophyll a-b binding protein 13 |
| EXP-CUCme.Bbz:1 | 7 | B-box zinc finger protein 24-like |
| P-CUCme.Bbz:1 | 8 | B-box zinc finger protein 24-like |
| L-CUCme.Bbz:1 | 9 | B-box zinc finger protein 24-like |
| EXP-Mt.Lhcb2:1:1 | 10 | Light harvesting complex protein b2 |
| P-Mt.Lhcb2-1:2:1 | 11 | Light harvesting complex protein b2 |
| L-Mt.Lhcb2-1:2:1 | 12 | Light harvesting complex protein b2 |
| EXP-Mt.PSII-T:1:1 | 13 | Photosystem II chloroplast precursor |
| P-Mt.PSII-T-1:2:1 | 14 | Photosystem II chloroplast precursor |
| L-Mt.PSII-T-1:2:1 | 15 | Photosystem II chloroplast precursor |

Example 2

Analysis of Regulatory Elements Driving GUS Expression in Stably Transformed Soybean Plants Soybean plants were transformed with vectors, specifically plant expression vectors, containing a test regulatory element driving expression of the ß-glucuronidase (GUS) transgene. The resulting plants were analyzed for GUS protein expression, to assess the effect of the selected regulatory elements on expression.

Soybean plants were transformed with the plant GUS expression constructs listed in Table 2. The regulatory elements were cloned into a base plant expression vector using standard methods known in the art. The resulting plant expression vectors contained a right border region from *Agrobacterium tumefaciens* (B-AGRtu.right border), a first transgene selection cassette used for selection of transformed plant cells that confers either resistance to either the herbicide glyphosate or the antibiotic, spectinomycin; a second transgene cassette to assess the activity of the regulatory element, which comprised an EXP sequence operably linked 5' to a coding sequence for ß-glucuronidase (GUS, GOI-Ec.uidA+St.LS1:1:1, SEQ ID NO: 17) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:3b:1, SEQ ID NO: 18); and a left border region from *Agrobacterium tumefaciens* (B-AGRtu.left border).

TABLE 2

Regulatory elements and corresponding GUS expression plasmid constructs

| Construct | EXP Description | SEQ ID NO: |
|---|---|---|
| pMON142244 | EXP-CUCme.Fe2:1 | 1 |
| pMON142241 | EXP-CUCme.CipLhcb:1 | 4 |
| pMON142216 | EXP-CUCme.Bbz:1 | 7 |
| pMON116798 | EXP-Mt.Lhcb2:1:1 | 10 |
| pMON116792 | EXP-Mt.PSII-T:1:1 | 13 |

Soybean plant cells were transformed using the binary transformation vector constructs described above by *Agrobacterium*-mediated transformation, using methods known in the art. The resulting transformed plant cells were induced to form whole soybean plants.

Histochemical GUS analysis was used for qualitative and quantitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues.

For quantitative analysis of GUS expression, total protein was extracted from selected tissues of transformed soybean plants. One microgram of total protein was used with the fluorogenic substrate 4-methylumbelliferyl-β-D-glucuronide (MUG) in a total reaction volume of 50 microliters. The reaction product, 4-methylumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 with Micromax Reader, with slit width set at excitation 2 nm and emission 3 nm. Values are provided in units of nmol GUS/hour/mg total protein.

The following tissues were sampled for GUS expression in the $R_0$ generation; Vn5 stage sink leaf, source leaf, and root; R1 stage petiole, source leaf, flower, and cotyledon; R3 stage pod and immature seed; and yellow pod stage embryo and cotyledon. Tables 3 and 4 below show the mean quantitative GUS expression for each of the sampled tissues driven by the regulatory elements presented in Table 2.

TABLE 3

Mean quantitative GUS expression in stably transformed soybean plants driven by regulatory elements derived from *Cucumis melo*

| Stage | Organ | EXP-CUCme.Fe2:1 | EXP-CUCme.CipLhcb:1 | EXP-CUCme.Bbz:1 |
|---|---|---|---|---|
| Vn5 | Sink Leaf | 391 | 159 | 100 |
| Vn5 | Root | 40 | 35 | 24 |
| Vn5 | Source Leaf | 431 | 120 | 185 |

TABLE 3-continued

Mean quantitative GUS expression in stably transformed soybean plants driven by regulatory elements derived from *Cucumis melo*

| Stage | Organ | EXP-CUCme.Fe2:1 | EXP-CUCme.CipLhcb:1 | EXP-CUCme.Bbz:1 |
|---|---|---|---|---|
| R1 | Petiole | 581 | 724 | 32 |
| R1 | Source Leaf | 600 | 357 | 41 |
| R1 | Flower | 290 | 111 | 30 |
| R5 | Cotyledon | 38 | 31 | 13 |
| R3 | Pod | 778 | 1199 | 85 |
| R3 | Immature Seed | 52 | 56 | 47 |
| Yellow Pod | Embryo | 23 | 28 | 38 |
| Yellow Pod | Cotyledon | 33 | 35 | 49 |

TABLE 4

Mean quantitative GUS expression in stably transformed soybean plants driven by regulatory elements derived from *Medicago truncatula*

| Stage | Organ | EXP-Mt.Lhcb2:1:1 | EXP-Mt.PSII-T:1:1 |
|---|---|---|---|
| Vn5 | Sink Leaf | 108 | 22 |
| Vn5 | Root | 21 | 11 |
| Vn5 | Source Leaf | 148 | 42 |
| R1 | Petiole | 153 | 83 |
| R1 | Source Leaf | 94 | 118 |
| R1 | Flower | 39 | 21 |
| R5 | Cotyledon | 13 | 9 |
| R3 | Pod | 85 | 33 |
| R3 | Immature Seed | 5 | 9 |
| Yellow Pod | Embryo | 4 | 0 |
| Yellow Pod | Cotyledon | 4 | 0 |

As can be seen in Tables 3 and 4, each of the regulatory elements has a unique pattern of expression in the tissues sampled. Both EXP-CUCme.Fe2:1 (SEQ ID NO: 1) and EXP-CUCme.CipLhcb:1 (SEQ ID NO: 4) express highly in the R3 pod and show the lowest level of expression in the R3 immature seed, Vn5 root, R5 cotyledon, and the yellow pod stage embryo and cotyledon. GUS expression driven by EXP-CUCme.Fe2:1 was also high in the Vn5 stage sink and source leaf and R1 stage petiole, source leaf, and flower. The regulatory element EXP-CUCme.Bbz:1 (SEQ ID NO: 7) demonstrated highest expression in the Vn5 stage sink and source leaf and R3 stage pod. GUS expression driven by EXP-Mt.Lhcb2:1:1 (SEQ ID NO: 10) was highest in the Vn5 stage source leaf and R1 petiole. EXP-Mt.PSII-T:1:1 (SEQ ID NO: 13) demonstrated highest expression in the R1 stage source leaf.

Each regulatory element provides a unique pattern of expression which can be used to optimally drive expression of different transgenes, depending on the desired tissue preference for expression.

Example 3

Enhancer Elements Derived from the Regulatory Elements

Enhancers are derived from the promoter elements presented as SEQ ID NOs: 2, 5, 8, 11, and 14. The enhancer element may be comprised of one or more cis regulatory elements that when operably linked 5' or 3' to a promoter element, or operably linked 5' or 3' to additional enhancer elements that are operably linked to a promoter, can enhance or modulate expression levels of a transcribable DNA molecule, or provide expression of a transcribable DNA molecule in a specific cell type or plant organ or at a particular time point in development or circadian rhythm. Enhancers are made by removing the TATA box or functionally similar elements and any downstream sequence from the promoters that allow transcription to be initiated from a promoter sequence, for example the sequences presented as SEQ ID NOs: 2, 5, 8, 11, and 14 or fragments thereof.

The TATA box in plant promoters is not as highly conserved as in some other Eukaryotic organisms. Therefore, in order to define a fragment as an enhancer, one first must identify the transcriptional start site (TSS) of the gene, wherein the 5' UTR is first transcribed. For example, the transcriptional regulatory element, EXP-Mt.Lhcb2:1:1 (SEQ ID NO: 10) is comprised of the promoter element, P-Mt.Lhcb2-1:2:1 (SEQ ID NO: 11), operably linked to the 5' UTR or leader element, L-Mt.Lhcb2-1:2:1 (SEQ ID NO: 12). Within the 1837 bp promoter element, P-Mt.Lhcb2-1:2:1 (SEQ ID NO: 11), the putative core TATA-like element is found within nucleotides 1798 through 1803. An enhancer fragment derived from the P-Mt.Lhcb2-1:2:1 could comprise nucleotides 1 through 1797 of SEQ ID NO: 11, resulting in the sequence presented as SEQ ID NO: 16 (E-Mt.Lhcb2). Enhancers derived from the promoter, P-Mt.Lhcb2-1:2:1 (SEQ ID NO: 11) can further comprise smaller fragments of E-Mt.Lhcb2 (SEQ ID NO: 16). The effectiveness of the enhancer elements derived from the promoter, P-Mt.Lhcb2-1:2:1 (SEQ ID NO: 11) is empirically determined by building a chimeric transcriptional regulatory element comprising an enhancer derived from the promoter, P-Mt.Lhcb2-1:2:1 (SEQ ID NO: 11), which is operably linked to a promoter and leader and used to drive expression of a transcribable DNA molecule such as GUS in stable or transient plant assay.

Further refinement of the enhancer element may be required and is validated empirically. In addition, position of the enhancer element relative to other elements within a chimeric transcriptional regulatory element is also empirically determined, since the order of each element within the chimeric transcriptional regulatory element may impart different effects, depending upon the relative positions of each element. Some promoter elements will have multiple TATA box or TATA box-like elements and potentially multiple transcription start sites. Under those circumstances, it may be necessary to first identify where the first TSS is located and then begin designing enhancers using the first TSS to prevent the potential initiation of transcription from occurring within a putative enhancer element.

Enhancer elements, derived from the promoter elements presented as SEQ ID NOs: 2, 5, 8, 11, and 14 are cloned using methods known in the art to be operably linked 5' or 3' to a promoter element, or operably linked 5' or 3' to additional enhancer elements that are operably linked to a promoter. Alternatively, enhancer elements can be cloned, using methods known in the art, to provide a larger enhancer element that is comprised of two or more copies of the enhancer and cloned using methods known in the art to be operably linked 5' or 3' to a promoter element, or operably linked 5' or 3' to additional enhancer elements that are operably linked to a promoter producing a chimeric transcriptional regulatory element. Enhancer elements can also be cloned using methods known in the art to be operably linked 5' to a promoter element derived from a different genus organism, or operably linked 5' or 3' to additional enhancer elements derived from other genus organisms that are operably linked to a promoter derived from either the same or different genus organism, resulting in a chimeric transcriptional regulatory element. A GUS expression plant transformation vector may be constructed using methods known in the art similar to the constructs described in Example 2 above in which the resulting plant expression vectors contain a right border region from Agrobacterium tumefaciens (B-AGRtu.right border), a first transgene selection cassette used for selection of transformed plant cells that confers resistance to the antibiotic, spectinomycin; and a second transgene cassette to test the enhancer element comprised of, the enhancer element operably linked 5' or 3' to a promoter element or operably linked 5' or 3' to additional enhancer elements that are in turn operably linked to a promoter which is operably linked 5' to a leader element, operably linked to a coding sequence for ß-glucuronidase (GUS, GOI-Ec.uidA+St.LS1:1:1, SEQ ID NO: 17) containing a processable intron derived from the potato light-inducible tissue-specific ST-LS1 gene (Genbank Accession: X04753), operably linked to a 3' termination region from the Gossypium barbadense E6 gene (T-Gb.E6-3b:3b:1, SEQ ID NO: 18), and a left border region from A. tumefaciens (B-AGRtu.left border). The resulting plasmids are used to transform soybean plants or other genus plants by the methods described above. Alternatively, protoplast cells derived from soybean or other genus plants are transformed using methods known in the art to perform transient assays GUS expression driven by a regulatory element comprising one or more enhancers is evaluated in stable or transient plant assays to determine the effects of the enhancer element on expression of a transcribable DNA molecule. Modifications to one or more enhancer elements or duplication of one or more enhancer elements may be performed based upon empirical experimentation and the resulting gene expression regulation that is observed using each regulatory element composition. Altering the relative positions of one or more enhancers in the resulting regulatory or chimeric regulatory elements may affect the transcriptional activity or specificity of the regulatory or chimeric regulatory element and is determined empirically to identify the best enhancers for the desired transgene expression profile within the corn plant or other genus plant.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a polynucleotide selected from the group consisting of:
   a) a polynucleotide with at least 95 percent sequence identity to SEQ ID NO: 5, wherein the polynucleotide has promoter activity;
   b) a polynucleotide with at least 97 percent sequence identity to SEQ ID NO: 4, wherein the polynucleotide has gene-regulatory activity;
   c) a polynucleotide comprising SEQ ID NO: 4 or 5; and
   d) a fragment comprising at least 150 contiguous nucleotides of SEQ ID NO: 5, wherein the fragment has promoter activity;
   wherein said DNA molecule is operably linked to a heterologous transcribable DNA molecule.

2. The recombinant DNA molecule of claim 1, wherein said polynucleotide has at least 97 percent sequence identity to SEQ ID NO: 5.

3. The recombinant DNA molecule of claim 2, wherein said polynucleotide has at least 99 percent sequence identity to SEQ ID NO: 4 or 5.

4. The recombinant DNA molecule of claim 3, wherein said polynucleotide comprises the DNA sequence of SEQ ID NO: 4 or 5.

5. The recombinant DNA molecule of claim 1, wherein the heterologous transcribable DNA molecule comprises a gene of agronomic interest.

6. The recombinant DNA molecule of claim 5, wherein the gene of agronomic interest confers herbicide tolerance in plants.

7. The recombinant DNA molecule of claim 5, wherein the gene of agronomic interest confers pest resistance in plants.

8. A transgenic plant cell comprising a recombinant DNA molecule comprising a polynucleotide selected from the group consisting of:
   a) a polynucleotide with at least 95 percent sequence identity to SEQ ID NO: 5, wherein the polynucleotide has promoter activity;
   b) a polynucleotide with at least 97 percent sequence identity to SEQ ID NO: 4, wherein the polynucleotide has gene-regulatory activity;
   c) a polynucleotide comprising SEQ ID NO: 4 or 5; and
   d) a fragment comprising at least 150 contiguous nucleotides of SEQ ID NO: 5, wherein the fragment has promoter activity;
   wherein said DNA molecule is operably linked to a heterologous transcribable DNA molecule.

9. The transgenic plant cell of claim 8, wherein said transgenic plant cell is a monocotyledonous plant cell.

10. The transgenic plant cell of claim 8, wherein said transgenic plant cell is a dicotyledonous plant cell.

11. A transgenic plant, or part thereof, comprising the recombinant DNA molecule of claim 1.

12. A progeny plant of the transgenic plant of claim 11, or a part thereof, wherein the progeny plant or part thereof comprises said recombinant DNA molecule.

13. A transgenic seed, wherein the seed comprises the recombinant DNA molecule of claim 1.

14. A method of producing a commodity product comprising obtaining the transgenic plant or part thereof according to claim 11 and producing the commodity product therefrom.

15. The method of claim 14, wherein the commodity product is protein concentrate, protein isolate, grain, starch, seeds, meal, flour, biomass, or seed oil.

16. A method of expressing a transcribable DNA molecule comprising obtaining the transgenic plant according to claim 11 and cultivating the plant, wherein the transcribable DNA is expressed.

* * * * *